United States Patent
Liu et al.

(10) Patent No.: US 9,284,235 B2
(45) Date of Patent: Mar. 15, 2016

(54) PROCESS FOR METHANOL COUPLED CATALYTIC CRACKING REACTION OF NAPHTHA USING A MODIFIED ZSM-5 MOLECULAR SIEVE CATALYST

(75) Inventors: Zhongmin Liu, Dalian (CN); Yingxu Wei, Dalian (CN); Yue Qi, Dalian (CN); Mao Ye, Dalian (CN); Mingzhi Li, Dalian (CN); Bing Li, Dalian (CN); Xiangao Wang, Dalian (CN); Changqing He, Dalian (CN); Xinde Sun, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 316 days.

(21) Appl. No.: 13/976,484

(22) PCT Filed: Jun. 24, 2011

(86) PCT No.: PCT/CN2011/076298
§ 371 (c)(1),
(2), (4) Date: Jul. 5, 2013

(87) PCT Pub. No.: WO2012/088852
PCT Pub. Date: Jul. 5, 2012

(65) Prior Publication Data
US 2014/0051900 A1   Feb. 20, 2014

(30) Foreign Application Priority Data
Dec. 28, 2010  (CN) .......................... 2010 1 0607910

(51) Int. Cl.
| | |
|---|---|
| *C07C 2/84* | (2006.01) |
| *B01J 29/40* | (2006.01) |
| *C10G 3/00* | (2006.01) |
| *C10G 11/05* | (2006.01) |
| *C07C 1/20* | (2006.01) |
| *C10G 11/10* | (2006.01) |
| *C10G 11/18* | (2006.01) |
| *B01J 37/00* | (2006.01) |

(52) U.S. Cl.
CPC .................. *C07C 2/84* (2013.01); *B01J 29/405* (2013.01); *B01J 37/0036* (2013.01); *B01J 37/0045* (2013.01); *C07C 1/20* (2013.01); *C10G 3/49* (2013.01); *C10G 11/05* (2013.01); *C10G 11/10* (2013.01); *C10G 11/18* (2013.01); *B01J 2229/186* (2013.01); *B01J 2229/42* (2013.01); *C07C 2523/10* (2013.01); *C07C 2527/14* (2013.01); *C07C 2529/40* (2013.01); *C10G 2300/1044* (2013.01); *C10G 2400/20* (2013.01); *C10G 2400/30* (2013.01); *Y02P 20/52* (2015.11); *Y02P 30/42* (2015.11)

(58) Field of Classification Search
CPC .............. C07C 2/82; C07C 2/84; C07C 2/86; C07C 2/76; C07C 2/864; C07C 4/02; C07C 4/06; C07C 4/08
USPC .......................... 585/640, 408, 407, 467, 469
See application file for complete search history.

(56) References Cited

U.S. PATENT DOCUMENTS

| | | |
|---|---|---|
| 3,767,567 A | 10/1973 | Tomita et al. |
| 4,172,816 A | 10/1979 | Pop et al. |
| 4,830,728 A | 5/1989 | Herbst et al. |
| 6,288,298 B1 | 9/2001 | Rodriguez et al. |
| 7,629,498 B2 * | 12/2009 | Brown et al. ................. 585/467 |
| 2009/0000988 A1 | 1/2009 | Brown et al. |

FOREIGN PATENT DOCUMENTS

| | | |
|---|---|---|
| CN | 1084431 A | 3/1994 |
| CN | 1302283 A | 7/2001 |
| CN | 1206319 C | 6/2004 |
| CN | 1241684 C | 6/2004 |
| EP | 0109059 B1 | 5/1984 |
| EP | 0568913 A2 | 11/1993 |
| EP | 2133319 A1 | 12/2009 |
| SU | 1298240 A1 | 3/1987 |

(Continued)

OTHER PUBLICATIONS

Yan et al. Catal Lett (2011) 141:691-698.*

(Continued)

*Primary Examiner* — In Suk Bullock
*Assistant Examiner* — Sharon Pregler
(74) *Attorney, Agent, or Firm* — Enshan Hong; VLP Law Group LLP

(57) ABSTRACT

The present invention provides a process for methanol coupled catalytic cracking reaction of naphtha using a modified ZSM-5 molecular sieve catalyst, comprising performing a co-feeding reaction of methanol and naphtha on the modified ZSM-5 molecular sieve catalyst to produce low carbon olefins and/or aromatic hydrocarbons. In the process, the modified ZSM-5 molecular sieve catalyst comprises, in term of weight percent, 25-80 wt % of a ZSM-5 molecular sieve, 15-70 wt % of a binder, and 2.2-6.0 wt % of lanthanum and 1.0-2.8 wt % of phosphorus loaded on the ZSM-5 molecular sieve. The naphtha comprises 63.8-89.5 wt % of saturated chain alkanes and 5.6-29.8 wt % of cyclic alkanes. The naphtha and methanol concurrently pass through the catalyst bed, which are reacted during contacting with the catalyst under a reaction condition of a reaction temperature of 550-670° C., a mass ratio of methanol to naphtha of 0.05-0.8, and a total mass space velocity of naphtha and methanol of 1.0-5 $h^{-1}$.

18 Claims, No Drawings

(56) References Cited

FOREIGN PATENT DOCUMENTS

| WO | 9951548 A1 | 10/1999 |
|---|---|---|
| WO | 99/57085 A1 | 11/1999 |
| WO | 01/64761 A2 | 9/2001 |

OTHER PUBLICATIONS

Yan H T et al: "Mixed Naphtha/Methanol Feed Used in the Thermal Catalytic/Steam Cracking (TCSC) Process for the Production of Propylene and Ethylene", Catalysis Letters, Kluwer Academic Publishers-Plenum Publishers, NE, vol. 141, No. 5, Dec. 14, 2010, pp. 691-698, XP019898090, ISSN: 1572-879X, DOI: 10.1007/S10562-010-0528-4.

European Extended Search Report dated Oct. 21, 2013 for European counterpart application No. EP 11853767.9.

Third Office Action dated Aug. 13, 2014 issued by the SIPO of China for the related Chinese patent application No. 201010607910.8.

First Office Action dated Jul. 27, 2014 issued by the Intellectual Property Office of Singapore for the related Singapore patent application No. 2013050976.

First Office Action dated Jun. 12, 2014 issued by the European patent office for the related European patent application No. 11 853 767.9.

Martin et al., Coupled Conversion of Methanol and C4 Hydrocarbons to Lower Olefins, Applied Catalysis, 50(1989), pp. 149-155.

International Search Report mailed on Oct. 20, 2011 to the applicant in connection with the PCT counterpart application PCT/CN2011/076298.

Written Opinion completed on Sep. 26, 2011 in connection with the CT counterpart application PCT/CN2011/076298.

Li Sen, et al. Study on the Interaction between Methanol and Naphtha under FCC conditions, Natural Gas Chemical Industry, 2008, vol. 33, No. 2, pp. 6-10.

Office Action issued Jun. 18, 2013 from SIPO of China in counterpart Chinese Application No. 201010607910.8.

* cited by examiner

PROCESS FOR METHANOL COUPLED CATALYTIC CRACKING REACTION OF NAPHTHA USING A MODIFIED ZSM-5 MOLECULAR SIEVE CATALYST

PRIORITY CLAIM

This is a U.S. national stage of application No. PCT/CN2011/076298, filed on Jun. 24, 2011. Priority is claimed on the following application: Country: China, Application No.: 20100607910.8, Filed: Dec. 28, 2010, the content of which is incorporated here by reference.

FIELD OF THE INVENTION

The invention relates to a process for methanol coupled catalytic cracking reaction of naphtha using a modified ZSM-5 molecular sieve catalyst.

BACKGROUND OF THE INVENTION

Olefins industry is an important basis for the development of the chemical industry. The production of low carbon olefins mainly employs the technical process of the high temperature water steam cracking of naphtha, wherein the reaction needs to be conducted under the condition of 800° C. or more, which is one of the processes consuming relatively large energy in the chemical industry. Recently, the price of the international crude oil keeps increasing, the cost of the raw material for olefin greatly increases, and the olefin corporations face more strict status. At the same time, the requirement in the international market for propylene presents the tendency of greatly increasing, and the product distribution of the traditional water steam cracking process which is dominated by ethylene could also not satisfy the increasing requirement of propylene in the market. The above factors promote the development of new olefin technology. The technology for producing ethylene and propylene by catalytic cracking at a relatively low temperature attracts broad attention. Meanwhile, catalytic cracking may results in a higher propylene yield, satisfying the increasing propylene requirement.

Naphtha is a mixed hydrocarbon product of $C_4$-$C_{12}$, the composition thereof is mainly saturated alkanes, which accounts for 50-95 wt % of the total compositions. These light hydrocarbons have a low carbon number and a high saturation degree. Currently, the commercial technology of producing low carbon olefins through cracking reaction from these light hydrocarbons is only known as the high temperature steam thermal cracking. Large amount of methane and coke are produced in the reaction. In order to solve the defects of high energy consumption and low raw material utilization, a series of catalytic cracking technologies are developed. Currently, the catalytic cracking technologies for saturated hydrocarbons and the naphtha dominated by saturated hydrocarbons are divided into two types of the fixed bed and the fluidized bed technologies.

In the fixed bed reaction process, the former Soviet Union develops a Kalium-Vanadium Vniios process (USSR Pat 1298240.1987). This catalyst uses potassium vanadate as an active component, $\alpha$-$Al_2O_3$ as a carrier, and oxides such as $B_2O_3$ and the likes as an aid. The semi-industry and industry experiments of naphtha catalytic cracking have been accomplished at 800° C. in the presence of steam. The yields of ethylene and propylene in this process are 38% and 14.5%, respectively, and the propylene/ethylene ratio is about 0.4. U.S. Pat. No. 3,767,567 uses $Al_2O_3$ and an oxide of any one of CaO, SrO and BaO as a catalyst for the catalytic cracking of naphtha. The reaction temperature is relatively high. With the generation of ethylene and propylene, a relatively large amount of dry gases, CO and $CO_2$ are produced. U.S. Pat. No. 4,172,816 uses Ag-MOR/$Al_2O_3$ as a catalyst, and conducts the reaction between 600 to 750° C. The yield of ethylene and propylene reaches 42%. U.S. Pat. No. 6,288,298 uses a silicon phosphorus aluminum molecular sieve SAPO-11 as a, catalyst for naphtha cracking, the light naphtha components cracking at 575° C., where the conversion is 39.2%, and the propylene selectivity in converted products reaches 56%. Patent ZL 02152479.3 of Dalian Institute of Chemical Physics, Chinese Academy of Sciences uses a modified molecular sieve as a catalyst, conducting the catalytic cracking of a naphtha raw material containing 60 wt % of a chain alkane and 30 wt % of a cyclic alkane which is reacted between 600-700° C., and the yield of ethylene and propylene reaches 45-50%.

The process for producing olefins by fluidized bed catalytic cracking disclosed in the Patents mainly uses the high-carbon atom number olefins as the cracking raw materials to conduct the production of low carbon olefins, but the patent technologies using the saturated hydrocarbons as the main cracking raw material is very few. WO099/57085 and WO01/64761 start from the raw material rich in olefin (20-70%), employ fluidized bed and a short residence time (1-10 s), and the raw material contacts with the molecular sieve-containing catalyst to produce $C_2$-$C_4$ olefins under the condition of a catalyst to raw material ratio of 2-10. EP 0109059 discloses a process of converting $C_4$-$C_{12}$ olefins to propylene. The employed catalyst is ZSM-5 or ZSM-11 molecular sieve with a silicon-aluminum ratio lower than 300, and the reaction is carried out at a space velocity higher than 50 $h^{-1}$, and a reaction temperature of 400-600° C. The total yield of ethylene and propylene is 36-44%, wherein the propylene yield is 30-40%. U.S. Pat. No. 4,830,728 introduces a fluidized bed catalytic cracking device used for maximizing the olefin yield. This device has two risers, wherein the heavy raw diesel oil is converted in one riser, while lighter olefins or naphtha raw material is cracked in another riser, and the adjustment of the condition for raw diesel oil riser may maximize the production of gasoline and olefins.

The above described catalytic cracking has such features that the alkaline catalytic cracking generally needs to be achieved at relatively high temperature. Although comparing with thermal cracking, the reaction temperature thereof is relatively reduced, it does not completely overcome the problem of high energy consumption and high methane production. Using the acidic molecular sieve catalyst may achieve the cracking of the raw material hydrocarbons at a relatively low temperature, but there is still the problem of system heat supplying.

The utilization of the coupling of different reaction processes is an efficient procedure for reducing the reaction thermal effect. Nowak et al. add C4 hydrocarbon during methanol conversion process to conduct the heat coupling (Appl. Catal. A 50(1989)149-155). At a reaction temperature of 600-700° C., when the molecule ratio of methanol to n-butane is 3:1, the reaction process on the HZSM-5 molecular sieve achieves the thermal neutralization. The coupled cracking of methanol and C6 hydrocarbons and naphtha also shows the promotion effect for the low carbon olefins production. The patent ZL 02152480.7 of Dalian Institute of Chemical Physics, Chinese Academy of Sciences suggests a coupled technical routine of producing low carbon olefins utilizing the catalytic cracking of the organic oxygen-containing compounds and the petroleum hydrocarbons. By coupling the reaction process having exothermic effect, the coupling of proper exothermic reaction of the organic oxygen-containing compounds causes that the cracking of petroleum hydrocarbons turns from a strong endothermic reaction process to a relatively strong or relatively weak endothermic reaction process, and may improve the yield of the low carbon olefins such as ethylene, propylene, and so on.

The methanol reaction and hydrocarbon cracking reaction mainly employ different catalyst systems. The present invention applies a modified ZSM-5 catalyst to the coupled reaction of the both, achieving the methanol coupled hydrocarbons cracking. Comparing with the separated naphtha cracking reaction, the modified ZSM-5 catalyzed methanol coupled reaction has a higher low carbon olefins yield and co-producing aromatic hydrocarbons.

SUMMARY OF THE INVENTION

An object of the present invention is to provide a process for methanol coupled catalytic cracking reaction of naphtha using a modified ZSM-5 molecular sieve catalyst, comprising performing a co-feeding reaction of methanol and naphtha on the modified ZSM-5 molecular sieve catalyst to produce low carbon olefins and/or aromatic hydrocarbons. By utilizing methanol coupled naphtha cracking reaction catalyzed by the modified ZSM-5 molecular sieve, it is capable of improving the catalytic cracking efficiency of naphtha, and producing low carbon olefins and aromatic hydrocarbons in high yield.

The catalyst provided in the present invention comprises a ZSM-5 molecular sieve, a binder and modifying elements. The ZSM-5 molecular sieve comprises 25-80 wt % of the total weight of the catalyst, wherein the silicon-aluminum ratio is in a range of 12-100. The binder may be alumina, silicon oxide or the mixture of the both, which comprises 15-70 wt % of the total weight of the catalyst. Lanthanum or phosphorus are used as the modified elements for the catalyst, wherein the lanthanum comprises 2.2-6.0 wt % of the total weight of the catalyst, and P comprises 1.0-2.8 wt % of the total weight of the catalyst. The modifying process may be exchanging or impregnation. The modified ZSM-5 molecular sieve catalyst may be used as a fluidized bed catalyst and a fixed bed catalyst. The modified ZSM-5 molecular sieve catalysts used for the fluidized bed catalyst and the fixed bed catalyst have different compositions. When the fluidized bed reactor is employed, the modified ZSM-5 molecular sieve catalyst comprises, in term of weight percent, 25-38.6 wt % of the ZSM-5 molecular sieve, 56-70 wt % of the binder, and the modifying elements, that is, 2.2-3.4 wt % of lanthanum and 2.0-2.8 wt % of phosphorus loaded on the ZSM-5 molecular sieve. When the fixed bed reactor is employed, the modified ZSM-5 molecular sieve catalyst comprises, in term of weight percent, 63-80 wt % of the ZSM-5 molecular sieve, 15-30 wt % of the binder, and the modifying elements, that is, 2.2-6.0 wt % of lanthanum and 1.0-2.8 wt % of phosphorus loaded on the ZSM-5 molecular sieve.

The production process for the modified ZSM-5 molecular sieve catalyst used for the fluidized bed is as follows.

1) A ZSM-5 molecular sieve from which the templating agent has been removed is exchanged with an ammonium nitrate solution at 80° C. for three times. After the exchange, it was calcined at 550° C. to obtain a H type ZSM-5 molecular sieve.

2) The H type ZSM-5 molecular sieve is exchanged with a lanthanum nitrate solution at 50° C. for 4 h, filtered, dried, and calcined at 550° C. in air for 6 h. The La modified ZSM-5 molecular sieve is exchanged with a phosphoric acid solution at 50° C. for 4 h, filtered, dried, and then calcined at 550° C. in air for 6 h.

3) The modified ZSM-5 molecular sieve is mixed with clay, silicon sol, aluminum sol, and deionized water so as to form a slurry whose solid content is 20-50 wt %. The slurry is aged for 3-10 h, and then subjected to spray forming so as to obtain a microsphere catalyst of 20-100 μm.

3) After the above described microsphere catalyst is calcined at 550° C. in air for 4-10 h, it is treated in a steam atmosphere at 700-850° C. for 3-15 h.

The production process for the modified ZSM-5 molecular sieve catalyst used for a fixed bed catalyst is as follows.

1) A as-synthesized ZSM-5 molecular sieve powder containing a synthesis templating agent is mixed with silicon sol and shaped, dried, and then calcined at 550° C. to remove the templating agent, and crushed into molecular sieve particles of 20-40 mesh.

2) The molecular sieve particles are exchanged with an ammonium nitrate solution at 80° C. for three times. After the exchanging, the molecular sieve particles are calcined at 550° C. so as to obtain H-type ZSM-5 molecular sieve particles.

3) The H-type ZSM-5 molecular sieve particles are impregnated with the modifying components, that is, a $La(NO_3)_3$ and $H_3PO_4$ solution, dried, calcined and then produced into the modified ZSM-5 catalysts.

Naphtha is one kind of the petroleum products during the petroleum refining and processing. The naphtha raw material used in the present invention comprises any one of a full-range naphtha, a light naphtha, and a raffinate oil, or any mixture thereof, wherein the full-range naphtha raw material has $C_4$-$C_{12}$ chain alkanes and cyclic alkanes as the main components, the light naphtha has $C_5$-$C_7$ chain alkanes as the main components, and the raffinate oil raw material has $C_4$-$C_9$ chain alkanes as the main components. The naphtha comprises 63.8-89.5 wt % of chain alkanes, 5.6-29.8 wt % of cyclic alkanes, 0.6-4.5 wt % of aromatic hydrocarbons and 1.9-4.3 wt % of olefins. The chain alkanes comprise linear and branched alkanes.

The specific compositions of various naphthas are shown in Tables 1-3.

TABLE 1

Compositions of naphtha: the full-range naphtha

| Carbon Numbers | Chain alkanes | Cyclic alkanes | Olefins | Aromatic hydrocarbons |
|---|---|---|---|---|
| $C_4$ | 1.4 | — | — | — |
| $C_5$ | 4.7 | — | — | — |
| $C_6$ | 9.1 | 6.7 | — | — |
| $C_7$ | 8.0 | 6.1 | 1.6 | — |
| $C_8$ | 12.8 | 6.9 | — | 0.9 |
| $C_9$ | 9.7 | 6.1 | — | 1.9 |
| $C_{10}$ | 7.9 | 1.7 | 0.3 | 1.3 |
| $C_{11}$ | 6.5 | 1.2 | — | 0.4 |
| $C_{12+}$ | 3.7 | 1.1 | — | — |
| Total | 63.8 | 29.8 | 1.9 | 4.5 |

TABLE 2

Compositions of naphtha: the light naphtha

| | Chain alkanes | Cyclic alkanes | Olefins | Aromatic hydrocarbons |
|---|---|---|---|---|
| $C_4$ | 1.5 | — | — | — |
| $C_5$ | 50.8 | 7.4 | — | — |

TABLE 2-continued

Compositions of naphtha: the light naphtha

|  | Chain alkanes | Cyclic alkanes | Olefins | Aromatic hydrocarbons |
|---|---|---|---|---|
| $C_6$ | 31.0 | 2.8 | — | 0.4 |
| $C_7$ | 3.4 | 3.4 | — | 0.5 |
| $C_8$ | — | 0.1 | — | — |
| Total | 85.4 | 13.7 | — | 0.9 |

TABLE 3

Compositions of naphtha: the raffinate oil

|  | Chain alkanes | Cyclic alkanes | Olefins | Aromatic hydrocarbons |
|---|---|---|---|---|
| $C_4$ | 0.2 | — | — | — |
| $C_5$ | 17.4 | 3.5 | 0.8 | — |
| $C_6$ | 44.6 | 0.6 | 2.0 | 0.2 |
| $C_7$ | 26.1 | 1.5 | 1.4 | 0.2 |
| $C_8$ | 1.2 | — | — | 0.2 |
| $C_9$ | 0.1 | — | — | — |
| Total | 89.5 | 5.6 | 4.3 | 0.6 |

In present invention, the reaction raw material is converted to low carbon olefins and aromatic hydrocarbons through the modified ZSM-5 catalyzed methanol coupled naphtha catalytic cracking, wherein the low carbon olefins comprise ethylene, propylene, and butylenes, and the aromatic hydrocarbons comprise benzene, toluene, and xylenes.

In present invention, a fluidized bed reaction device and a fixed bed reaction device are used to conduct the catalytic cracking of a saturated hydrocarbon raw material, wherein the fluidized bed comprising a fixed-fluidized bed and a circulating fluidized bed.

In a fluidized bed reaction, the fluidized bed reactor is charged with a fluidized bed catalyst having a particle size in a range of 20 to 100 μm, and the catalyst is fluidized in the reactor. The co-fed naphtha and methanol raw material are added from the bottom of the reactor, while a diluting gas is introduced so as to reduce the partial pressure of the reaction materials and help the fluidization of the catalyst. The diluting gas may be an inert gas or steam, most preferably the steam. Naphtha, methanol, and the diluting gas may be mixed with the catalyst and may fluidize the catalyst in the reactor, and be converted into products such as low carbon olefins, aromatic hydrocarbons, and the like under the reaction condition. The reaction temperature ranges in 580 to 670° C., the reaction pressure is 0.1-0.3 MPa, and the mass space velocity of naphtha and methanol is 0.3-5 $h^{-1}$.

In a fixed bed reaction, naphtha and methanol are co-fed together with steam into the reactor, and contacted with the fixed bed catalyst and reacted to produce low carbon olefins and aromatic hydrocarbons. The mass ratio between methanol and naphtha is 0.05-0.8, the ratio of the steam and the raw material (naphtha and methanol) is 0.1-0.5, the range of the reaction temperature is 560-670° C., the mass space velocity of naphtha is 0.3-5 $h^{-1}$, the mass space velocity of methanol is 0.01-4 $h^{-1}$, and the total mass space velocity of naphtha and methanol is 1.0-5 $h^{-1}$.

In the present invention, a modified ZSM-5 molecular sieve catalyst is applied to the methanol coupled naphtha catalytic cracking reaction. By the coupled reaction of methanol and naphtha on the catalyst, the reaction efficiency of naphtha cracking is improved, while the exothermic effect of the methanol conversion may also provide heat for the strong endothermic cracking reaction, reducing the reaction temperature, and solving the defects in the present olefin technologies such as high reaction temperature, high methane and coke yield, low raw material utilization, and so on, thus achieving the production of low carbon olefins under the condition of a relatively low reaction temperature, reducing the reaction energy consumption, improving the production efficiency of the low carbon olefins, while capable of co-producing aromatic hydrocarbons.

In the present invention, in the methanol coupled naphtha catalytic cracking reaction catalyzed by the modified ZSM-5, the yield of ethylene is 10-25 wt %, the yield of propylene is 15-28 wt %, the yield of butylene is 5-15 wt %, the yield of BTX (benzene, toluene, and xylenes) is 4-20 wt %, wherein the producing ratio of ethylene and propylene in the product and the producing ratio of low carbon olefins (ethylene, propylene, and butylenes) and aromatic hydrocarbons may be adjusted by the active components of the modified catalyst and the operation conditions of the reaction (reaction temperature, space velocity, and water/oil ratio, and so on).

DETAILED DESCRIPTION OF THE INVENTION

The present invention is described in detail in the following Examples.

In the present invention, the unmodified ZSM-5 molecular sieve used is purchased from Nankai Catalyst Factory.

In the present invention, the chemicals used are all commercially available products.

Example 1

This Example illustrates the preparation of a modified ZSM-5 fluidized bed catalyst.

500 g of a ZSM-5 molecular sieve from which the templating agent had been removed was exchanged with 2000 mL of an ammonium nitrate solution with a concentration of 1N at 80° C. for three times. After the exchange, the ZSM-5 molecular sieve was calcined at 550° C. to obtain a H-type ZSM-5 molecular sieve.

100 g of the H-type ZSM-5(Si/Al=12.5) molecular sieve was exchanged with 200 mL of a $La(NO_3)_3$ solution with a concentration of 0.15 mol/L at 50° C. for 4 h, and the exchanged molecular sieve was filtered, dried, and then calcined at 550° C. in air for 6 h. 100 g of the La modified ZSM-5 molecular, sieve was exchanged with 200 mL of an aqueous $H_3PO_4$ solution with a concentration of 0.25 mol/L at 50° C. for 4 h, and the exchanged molecular sieve was filtered, dried, and calcined at 550° C. in air for 6 h.

25 g of the above described La and P modified ZSM-5 sample was mixed with 50 g of kaolin (containing 15 wt % of water), 8 g of silicon sol (the $SiO_2$ content was 25 wt %), 138 g of aluminum sol (the alumina content was 22 wt %), and 128 g of deionized water so as to form a slurry, the solid content of the slurry was 25 wt %. 150 g of the slurry was aged at room temperature for 4 h and passed through a colloid mill twice, and then subjected to spray forming so as to obtain a microsphere catalyst with a particle size of 20-100 μm, that is, modified ZSM-5-fluidized bed A.

500 g of a ZSM-5 molecular sieve from which the templating agent had been removed was exchanged with 2000 mL of an ammonium nitrate solution with a concentration of 1N at 80° C. for three times. After the exchange, the ZSM-5 molecular sieve was calcined at 550° C. to obtain a H-type ZSM-5 molecular sieve.

100 g of the H-type ZSM-5(Si/Al=12.5) molecular sieve was exchanged with 200 mL of a La(NO$_3$)$_3$ solution with a concentration of 0.27 mol/L at 50° C. for 4 h, and the exchanged molecular sieve was filtered, dried, and then calcined at 550° C. in air for 6 h. 100 g of the La modified ZSM-5 molecular sieve was exchanged with 200 mL of an aqueous H$_3$PO$_4$ solution with a concentration of 0.20 mol/L at 50° C. for 4 h, and the exchanged molecular sieve was filtered, dried, and calcined at 550° C. in air for 6 h.

38.6 g of the above described La and P modified ZSM-5 sample was mixed with 50 g of kaolin (containing 15 wt % of water), 8 g of silicon sol (the SiO$_2$ content was 25 wt %), 30.5 g of aluminum sol (the alumina content was 22 wt %), and 213 g of deionized water so as to form a slurry, the solid content of the slurry was 25 wt %. 200 g of the slurry was aged at room temperature for 4 h and passed through a colloid mill twice, and then subjected to spray forming so as to obtain a microsphere catalyst with a particle size of 20-100 μm, that is, modified ZSM-5-fluidized bed B.

After the above described microsphere catalysts were calcined at 550° C. in air for 6 h, they were treated in steam atmosphere at 800° C. for 10 h.

The compositions of the specific modified ZSM-5 microsphere catalysts are as shown in Table 4.

TABLE 4

The compositions of the modified ZSM-5 fluidized bed catalysts

| Catalyst | The Si/Al ratio of HZSM-5 | Compositions (wt %) | | | |
|---|---|---|---|---|---|
| | | ZSM-5 | SiO$_2$—Al$_2$O$_3$ | P | La |
| Modified ZSM-5-fluidized bed A | 12 | 25.0 | 70.0 | 2.8 | 2.2 |
| Modified ZSM-5-fluidized bed B | 25 | 38.6 | 56.0 | 2.0 | 3.4 |

Example 2

This Example illustrates the effect of the catalytic cracking reaction of naphtha coupled with methanol catalyzed by the modified ZSM-5 in a fixed-fluidized bed.

The naphtha used in this Example comprised a full-range naphtha, a light naphtha and a raffinate oil, the specific compositions thereof were shown in Table 5.

The catalyst prepared in Example 1 was used as the reaction catalyst. 10 g of the catalyst was charged into a fixed-fluidized bed reactor, and treated in air atmosphere at 650° C. for 1 h, and then purged with nitrogen atmosphere for 0.5 h, and the reactor temperature was adjusted to a reaction temperature of 630° C. Naphtha, methanol, and water were introduced into a pre-heater through a feeding pump. The raw materials were vaporized in the pre-heater at 300° C. and then introduced into the fixed-fluidized bed reactor in which methanol, naphtha and steam were contacted with the catalyst and the catalyst was fluidized, wherein the total space velocity of the feeding naphtha and methanol were 2 h$^{-1}$; the mass ratio of water:(naphtha+methanol) was 0.15; the mass ratio of methanol:naphtha was 0.2; and the reaction pressure was 0.1 MPa. The reaction product was on-line analyzed by employing a Varian3800 gas chromatograph (Varian) and Pona capillary chromatographic column (Varian). The reaction results were shown in Tables 6 and 7.

TABLE 5

Compositions of naphtha

| Naphtha | Carbon Number Distribution | Chain alkanes (%) | Cyclic alkanes (%) | Olefins (%) | Aromatic hydrocarbons (%) |
|---|---|---|---|---|---|
| Full-range naphtha | C$_4$-C$_{12}$ | 63.8 | 29.8 | 1.9 | 4.5 |
| Light naphtha | C$_4$-C$_8$ | 85.4 | 13.7 | — | 0.9 |
| Raffinate oil | C$_4$-C$_9$ | 89.5 | 5.6 | 4.3 | 0.6 |

TABLE 6

Methanol coupled naphtha cracking reaction catalyzed by modified ZSM-5-fluidized bed A in a fixed-fluidized bed

| Raw material | Full-range naphtha | Light naphtha | Raffinate oil |
|---|---|---|---|
| | Product yields, wt % | | |
| Ethylene | 18 | 20 | 20 |
| Propylene | 22 | 24 | 25 |
| Butylenes | 9 | 9 | 10 |
| BTX | 13 | 7 | 8 |

TABLE 7

Methanol coupled naphtha cracking reaction catalyzed by modified ZSM-5-fluidized bed B in fixed-fluidized bed

| Raw material | Full-range naphtha | Light naphtha | Raffinate oil |
|---|---|---|---|
| | Product yields, wt % | | |
| Ethylene | 19 | 21 | 20 |
| Propylene | 23 | 24 | 28 |
| Butylenes | 10 | 11 | 10 |
| BTX | 14 | 8 | 9 |

Comparative Example 1

This Comparative Example illustrates the effect of the catalytic cracking reaction of only naphtha catalyzed by the modified ZSM-5 in a fixed-fluidized bed.

A catalyst of ZSM-5-fluidized bed A prepared in Example 1 was employed as the reaction catalyst, and the reaction raw materials in Example 2 was modified from naphtha and methanol to naphtha so that the reaction raw material was only naphtha without adding methanol, and the space velocity for feeding naphtha was 2 h$^{-1}$, the mass ratio of water:naphtha was 0.15, and other reaction conditions and analysis conditions were the same as those in Example 2. The reaction results were shown in Table 8.

TABLE 8

Cracking reaction of only naphtha catalyzed by modified ZSM-5-fluidized bed A in a fixed-fluidized bed

| Raw material | Full-range naphtha | Light naphtha | Raffinate oil |
|---|---|---|---|
| | Product yield, wt % | | |
| Ethylene | 15 | 17 | 17 |
| Propylene | 20 | 20 | 21 |
| Butylene | 9 | 10 | 11 |
| BTX | 11 | 5 | 6 |

Example 3

This Example illustrates the catalytic cracking reaction of methanol coupled full-range naphtha in a fixed-fluidized bed under the condition of different mass ratios of methanol to naphtha.

The catalyst ZSM-5-fluidized bed A prepared in Example 1 was used as the reaction catalyst, full-range naphtha was used as the naphtha, and the mass ratio of methanol to naphtha was adjusted as 0.05, 0.4, and 0.8. Other reaction conditions and analysis conditions were the same as those in Example 2. The reaction results are as shown in Table 9.

TABLE 9

The methanol coupled naphtha cracking reaction in fixed-fluidized bed under the condition of different mass ratios of methanol to naphtha

| | Methanol/naphtha (mass ratio) | | |
|---|---|---|---|
| | 0.05 | 0.4 | 0.8 |
| | Product yields, wt % | | |
| Ethylene | 15 | 22 | 23 |
| Propylene | 21 | 22 | 24 |
| Butylenes | 9 | 7 | 7 |
| BTX | 12 | 15 | 17 |

Example 4

This Example illustrates the methanol coupled catalytic cracking reaction of full-range naphtha catalyzed by the modified ZSM-5 molecular sieve in a fixed-fluidized bed under the condition of different reaction temperatures.

The catalyst ZSM-5-fluidized bed A prepared in Example 1 was used as the reaction catalyst, the naphtha was full-range naphtha, the reaction temperature was 550° C., 600° C., and 670° C., respectively, and other reaction conditions and analysis conditions were the same as those in Example 2. The reaction results are as shown in Table 10.

TABLE 10

The methanol coupled naphtha cracking reaction in fixed-fluidized bed under the condition of different reaction temperatures

| | Reaction temperature (° C.) | | |
|---|---|---|---|
| | 550 | 600 | 670 |
| | Product yields, wt % | | |
| Ethylene | 15 | 17 | 22 |
| Propylene | 21 | 23 | 25 |
| Butylenes | 13 | 10 | 7 |
| BTX | 8 | 11 | 16 |

Example 5

The present Example illustrates the catalytic cracking reaction of methanol coupled full-range naphtha catalyzed by the modified ZSM-5 molecular sieve in a circulating fluidized bed.

Full-range naphtha was used as the naphtha. The catalyst ZSM-5-fluidized bed A prepared in Example 1 is used as the reaction catalyst. 5 kg of the catalyst was charged into a fluidized bed reaction system, and was treated at 650° C. in air atmosphere for 1 h, and then purged with nitrogen gas for 0.5 h, and the reactor temperature was adjusted to a reaction temperature of 650° C., while the catalyst was adjusted to be a inventory of 1.0 kg in the reactor. Naphtha, methanol, and water were introduced into a pre-heater through a feeding pump. The raw materials were vaporized in the pre-heater at 300° C. and then introduced into the fixed-fluidized bed reactor to be contacted with the catalyst and the catalyst was fluidized. The space velocity of the reaction was $1.0\ h^{-1}$, the water/naphtha mass ratio was 0.2, the methanol/naphtha mass ratio was 0.1-0.31, and the reaction pressure was 0.1 MPa. The reaction product was on-line analyzed by employing a Varian3800 gas chromatograph (Varian) and Pona capillary chromatographic column (Varian). The reaction results were shown in Table 11.

TABLE 11

The methanol coupled naphtha cracking reaction under the condition of different methanol/naphtha mass ratios in a circulating fluidized bed

| | Methanol/naphtha (mass ratio) | | |
|---|---|---|---|
| | 0.1 | 0.16 | 0.31 |
| | Product yields, wt % | | |
| Ethylene | 18 | 19 | 20 |
| Propylene | 21 | 23 | 24 |
| Butylenes | 9 | 10 | 9 |
| BTX | 11 | 12 | 10 |

Example 6

This Example illustrates the preparation of the modified ZSM-5 fixed bed catalyst.

A ZSM-5 molecular sieve raw powder containing a synthesis templating agent was mixed with silicon sol and aluminum sol, shaped, dried, and then calcined at 550° C. to remove the templating agent, and crushed into molecular sieve particles of 20-40 mesh. The molecular sieve particles were exchanged with an ammonium nitrate solution at 80° C. for three times. After the exchanging, the molecular sieve particles were calcined at 550° C. so as to obtain H-type ZSM-5 molecular sieve particles. The molecular sieve particles were impregnated with the modifying components, that is, a $La(NO_3)_3$ and $H_3PO_4$ solution, dried, calcined and then produced into the modified ZSM-5 catalysts. The compositions of the fixed bed catalysts obtained through different preparation and modifying manners were shown in Table 10.

TABLE 10

The compositions of the modified ZSM-5 fixed bed catalyst

| Catalyst | Si/Al ratio of HZSM-5 | Compositions (wt %) | | | |
|---|---|---|---|---|---|
| | | HZSM-5 | $SiO_2$—$Al_2O_3$ | P | La |
| Modified ZSM-5-fixed bed A | 23 | 80.0 | 15.0 | 2.8 | 2.2 |
| Modified ZSM-5-fixed bed B | 50 | 79.6 | 15.0 | 2.0 | 3.4 |
| Modified ZSM-5-fixed bed C | 100 | 63.0 | 30.0 | 1.0 | 6.0 |

Example 7

This Example illustrates the reaction effect of the modified ZSM-5 catalyst in the catalytic cracking of methanol coupled naphtha in a fixed bed.

Full-range naphtha and methanol were used as the raw material. The catalyst prepared in Example 6 was used as the reaction catalyst. 5 g of the catalyst was charged into a fixed bed reactor, and treated in air atmosphere at 670° C. for 1 h, and then purged in the nitrogen atmosphere for 0.5 h, and the reactor temperature was adjusted to a reaction temperature of 630° C. Naphtha, methanol, and water were introduced into a pre-heater through a feeding pump. The raw materials were vaporized in the pre-heater at 300° C. and then introduced into the fixed-fluidized bed reactor to be contacted with the catalyst. The total feeding space velocity of naphtha and methanol was 5.0 $h^{-1}$, the mass ratio of water:(naphtha+methanol) was 0.5, the mass ratio of methanol:naphtha was 0.2, and the reaction pressure was 0.1 MPa. The reaction product was on-line analyzed by employing a Varian3800 gas chromatograph (Varian) and Pona capillary chromatographic column (Varian). The reaction results are shown in Table 11.

TABLE 11

The methanol coupled naphtha cracking reaction catalyzed by modified ZSM-5 in fixed bed

| Catalyst | Modified ZSM-5-fixed bed A | Modified ZSM-5-fixed bed B | Modified ZSM-5-fixed bed C |
|---|---|---|---|
| | Product yields, wt % | | |
| Ethylene | 21 | 20 | 18 |
| Propylene | 26 | 27 | 28 |
| Butylenes | 9 | 8 | 10 |
| BTX | 14 | 14 | 10 |

Example 8

This Example illustrates the reaction effect of the modified ZSM-5 catalyst in the catalytic cracking of methanol coupled mixed naphtha in a fixed bed.

The naphtha was a mixture of two or three of a full-range naphtha, a light naphtha, and a raffinate oil. The catalyst ZSM-5-fluidized bed A prepared in Example 1 was used as the reaction catalyst, and other reaction conditions and analysis conditions were the same as those in Example 7. The reaction results were shown in Table 12.

TABLE 12

The methanol coupled mixed naphtha cracking reaction catalyzed by modified ZSM-5 in a fixed bed

| Raw material | Mixed raw material 1 (50 wt % full-range naphtha + 50% raffinate oil) | Mixed raw material 2 (40 wt % full-range naphtha + 30 wt % light naphtha 30% raffinate oil) |
|---|---|---|
| | Product yields, wt % | |
| Ethylene | 22 | 23 |
| Propylene | 27 | 26 |
| Butylene | 10 | 12 |
| BTX | 10 | 8 |

What is claimed is:

1. A process for a methanol coupled catalytic cracking reaction of naphtha using a modified ZSM-5 molecular sieve catalyst, comprising:
   passing a feedstream comprising the methanol and the naphtha to a reactor and contacting the feedstream with the modified ZSM-5 molecular sieve catalyst at reaction conditions to produce an effluent comprising low carbon olefins and/or aromatic hydrocarbons;
   wherein the modified ZSM-5 molecular sieve catalyst comprises, in term of weight percent, 25-80 wt % of a ZSM-5 molecular sieve, 15-70 wt % of a binder, 2.2-6.0 wt % of lanthanum and 1.0-2.8 wt % of phosphorus;
   wherein the naphtha comprises 63.8-89.5 wt % of saturated chain alkanes and 5.6-29.8 wt % of cyclic alkanes; and
   wherein the naphtha comprises hydrocarbons with a carbon number distribution range of $C_4$-$C_{12}$.

2. The process according to claim 1, wherein the naphtha and the methanol are concurrently passed through a catalyst bed at a reaction temperature of 550-670° C.

3. The process according to claim 1, wherein the mass ratio of the methanol to the naphtha is 0.05-0.8.

4. The process according to claim 1, wherein the naphtha and methanol are fed to the reactor at a total mass space velocity of 1.0-5 $h^{-1}$.

5. The process according to claim 1, wherein the naphtha is any one of a full-range naphtha, a light naphtha, and a raffinate oil, or any mixture thereof.

6. The process according to claim 1, wherein the naphtha further comprises 0.6-4.5 wt % of aromatic hydrocarbons and 1.9-4.3 wt % of olefins.

7. The process according to claim 1, wherein the reactor is a fluidized bed reactor or a fixed bed reactor.

8. The process according to claim 7, wherein when the fluidized bed reactor is employed, and the modified ZSM-5 molecular sieve catalyst comprises, in term of weight percent, 25-38.6 wt % of the ZSM-5 molecular sieve, 56-70 wt % of the binder, 2.2-3.4 wt % of lanthanum, and 2.0-2.8 wt % of phosphorus.

9. The process according to claim 7, wherein when the fixed bed reactor is employed, and the modified ZSM-5 molecular sieve catalyst comprises, in term of weight percent, 63-80 wt % of the ZSM-5 molecular sieve, 15-30 wt % of the binder, 2.2-6.0 wt % of lanthanum, and 1.0-2.8 wt % of phosphorus.

10. The process according to claim 7, wherein the fluidized bed reactor includes a fixed-fluidized bed and a circulating fluidized bed.

11. The process according to claim 1, wherein the low carbon olefins include ethylene, propylene, and butylene.

12. The process according to claim 1, wherein the aromatic hydrocarbons include benzene, toluene, and xylene.

13. The process according to claim 1, wherein the range of the silicon-aluminum ratio of the ZSM-5 molecular sieve is 12-100.

14. The process according to claim 1, wherein the binder is silicon oxide, alumina, or the mixture thereof.

15. The process according to claim 8, wherein the range of the silicon-aluminum ratio of the ZSM-5 molecular sieve is 12-100.

16. The process according to claim 9, wherein the range of the silicon-aluminum ratio of the ZSM-5 molecular sieve is 12-100.

17. The process according to claim 8, wherein the binder is silicon oxide, alumina, or the mixture thereof.

18. The process according to claim 9, wherein the binder is silicon oxide, alumina, or the mixture thereof.

* * * * *